United States Patent
Wietelmann et al.

(10) Patent No.: US 6,544,446 B2
(45) Date of Patent: Apr. 8, 2003

(54) METHOD OF PREPARING MAGNESIUM ALCOHOLATES

(75) Inventors: Ulrich Wietelmann, Friedrichsdorf (DE); Dieter Hauk, Friedberg (DE); Peter Rittmeyer, Sulzbach/Taunus (DE)

(73) Assignee: Chemetall GmbH, Frankfurt am Main (DE)

( * ) Notice: Subject to any disclaimer, the term of this patent is extended or adjusted under 35 U.S.C. 154(b) by 0 days.

(21) Appl. No.: 09/988,804

(22) Filed: Nov. 20, 2001

(65) Prior Publication Data

US 2002/0095060 A1 Jul. 18, 2002

(30) Foreign Application Priority Data

Nov. 23, 2000 (DE) .......................................... 100 58 286

(51) Int. Cl.$^7$ ............................................... C07C 31/30
(52) U.S. Cl. ...................................................... 260/665
(58) Field of Search ................................. 568/700, 840, 568/851

(56) References Cited

U.S. PATENT DOCUMENTS

| | | | | | |
|---|---|---|---|---|---|
| 2,570,058 | A | * | 10/1951 | Hunter | |
| 3,657,361 | A | * | 4/1972 | Lenz et al. | 568/672 |
| 4,178,300 | A | * | 12/1979 | van den Berg | 554/71 |
| 4,748,283 | A | * | 5/1988 | Kamienski | 556/170 |
| 5,468,705 | A | * | 11/1995 | Rauleder et al. | 106/287.23 |

* cited by examiner

Primary Examiner—Jean F. Vollano
(74) Attorney, Agent, or Firm—Fulbright & Jaworski L.L.P.

(57) ABSTRACT

A method of preparing magnesium alcoholates $Mg(OR)_2$ (where R=alkyl residue having 2 to 10 carbon atoms) is described. Addition products of 1,3-dienes to magnesium metal in a polar, aprotic solvent are reached with an alcohol R—OH.

20 Claims, No Drawings

METHOD OF PREPARING MAGNESIUM ALCOHOLATES

Magnesium alcoholates (or magnesium alkoxides) $Mg(OR)_2$, R=alkyl, are solids sensitive to hydrolysis which can be used in organic synthesis as selective bases and as constituents of polymerising catalysts. Due to the ability of the bivalent magnesium cation to form stable chelate complexes with carbonyl compounds, magnesium methylate for example is used as a selective carbonyl condensing agent.

Magnesium methylate is prepared by reacting magnesium metal with dry methanol (D. Caine, "Magnesium Methoxide" in: L. Paquette (ed.), *Encyclopedia of Reagents for Organic Synthesis*, 3204–3205). The magnesium salts of the "higher" primary alcohols, i.e. alcohols with $\geq 2$ carbon atoms, do not react directly with pure alcohols under normal conditions. In fact catalysts are required to set the reaction in motion (H. Lund and J. Bjerrum, *Chem. Ber.* (*B*), 64, 210 (1931); U.S. Pat. No. 2,287,088; DE 1,230,004 (Rheinpreußen 1967)):

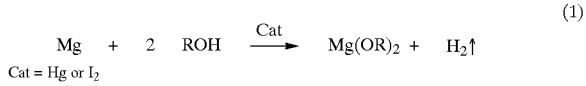

(1)

Cat = Hg or $I_2$

Another possible way of accelerating the reaction is to perform the preparation under pressure at the higher temperatures which are then possible. The ethylate and n-propylate for example can be prepared in a few hours at approximately 130° C. at a pressure of about 10 atm. gauge (DE OS 2261386).

As is described in the literature (H. Thoms, M. Epple, H. Viebrock, A. Reller, *J. Mater. Chem.* 1995, 5 (4), 589–594) and as has been confirmed by our own experiments, direct synthesis starting with Mg metal and the particular alcohol (ROH) does not work where R=branched alkyl residue (e.g. propan-2-ol, tert. butanol, octan-2-ol).

A disadvantage of Mg alcoholate synthesis by (1) is that it is confined to R=methyl if pure alcohol is used. It is true that the Mg salts of fairly long-chain primary alcohols can also be prepared from the particular alcohol and Mg metal, but only if catalysts are used. The catalyst represents an additional cost factor and causes contamination of the alcoholate. There are serious environmental and safety-at-work objections to using mercury. Expensive production apparatus is required for synthesis under pressure.

It is also known that sterically demanding substituted magnesium alcoholates can be prepared from bis(organo) magnesium $R_2Mg$ and alcohols (H. Thoms, M. Epple, A. Reller, *Solid State Ionics* 101–103 (1997), 79–84):

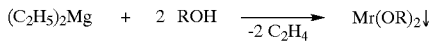

R = saturated alkyl, e.g. ethyl

The main disadvantage of synthesis route (2) lies in the fact that relatively expensive dialkyl magnesium compounds, such as $Et_2Mg$ for example, have to be used as starting materials. Dialkyl compounds where R=saturated alkyl residue are in fact usually prepared from Grignard compounds RMgX and organolithium compounds as follows:

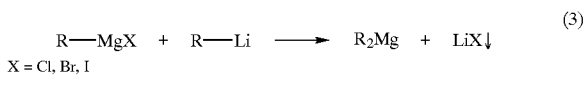

(3)

X = Cl, Br, I or by the addition of olefins to active magnesium hydride as follows

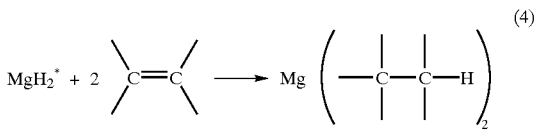

(4)

*activated

In the case of reaction (3), the high costs are caused by the price of the organolithium compound and the Grignard compound and by the salt wastes (LiX) that have to be disposed of. Also, the resulting magnesium alcoholate is contaminated with lithium residues from the preceding R—Li stage, which detracts from the purity (and hence the selectivity in applications as a catalyst) of the $Mg(OR)_2$ end product. A disadvantage of reaction (4) is that active magnesium hydride is not commercially available.

An object of the invention is to overcome the disadvantages of the prior art and, in particular, to provide a method which allows various magnesium alcoholates, inducting the magnesium alcoholates of secondary and tertiary alcohols, to be prepared from generally available raw materials.

This object is achieved by reacting addition products of 1,3-dienes to magnesium metal in a polar, aprotic solvent with an alcohol R—ON (R=alkyl residue with 2 to 10 carbon atoms). The insoluble Mg alcoholate $Mg(OR)_2$ which is formed can then be isolated by a solid/liquid separating operation.

Surprisingly, it was found that the addition products of Mg metal and 1,3-dienes are sufficiently reactive to react fast and quantitatively with even only sparingly acid alcohols, such as tert, butanol for example.

Described in the literature (K. Nützel, in Houben-Weyl, Methoden der Organischen Chemie, Vol.XIII/2a, p.210–214, G. Thieme Verlag, Stuttgart 1973) is the addition product of isoprene and magnesium which is formed in the form of a 2:1 adduct

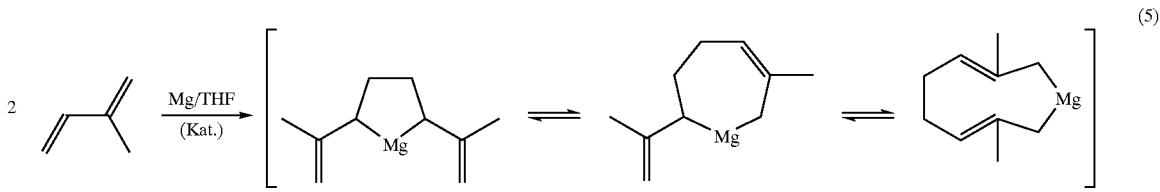

(5)

Surprisingly, it was further found that in the reaction of 1,3-diene with Mg metal to form the addition product, less than twice the molar amount of 9,3-diene is required to fully decompose a given amount of magnesium. Depending on the reaction conditions, the molar ratio of 1,3-diene to Mg in the addition product is between 2:1 and 1:1.

The reaction between the 1,3-diene and magnesium takes place in a temperature range of between 0 and 100° C. and preferably at approximately 10 to 70° C. The Mg metal used preferably has a high surface area, e.g. is in chip, granular or powder form.

The 1,3-diene used is preferably 1,3-butadiene, isoprene, dimethyl butadiene and/or 1,3-cyclohexadiene.

The solvents used are polar, aprotic solvents, preferably ethers, and a particular preference is for THF, 2-methyl-THF, dimethyl ether or dimethoxyethane. The polar, aprotic solvent can be mixed with liquid hydrocarbons such as pentane, hexane, cyclohexane, heptane, octane, toluene or xylene.

Where the particularly preferred solvent THF is used, the reaction preferably takes place under reflux conditions, the boiling point being dependent on the nature of the 1,3-diene. Where 1,3-butadiene is used, it is advisable for the reaction to be carried out at a slightly raised pressure (up to 1,5 bar) or for a cooler operating at temperatures of <–10° C. to be used to ensure that no appreciable losses of butadiene occur. Where isoprene is used, operations can take place at normal pressure and at temperatures of between 50 and 65° C.

To accelerate the reaction, a polynuclear aromatic compound, such as anthracene, phenanthrene or biphenyl for example, can be added in catalytic quantities (preferably 0.01 to 5 mol % relative to the quantity of Mg) as a metal phase transfer catalyst. Anthracene has been found to be a particularly advantageous catalyst. It is particularly advantageous (to prevent slowing up of the reaction) for the catalyst to be added to the suspension of magnesium metal in the aprotic solvent before the 1,3-diene is measured in. The reason is that the magnesium-anthracene adduct is orange In colour and it is easy for the operator to conclude from the production of the adduct, which is clearly apparent visually, that the reaction mixture is inert (i.e. totally free of water) and the metal is present in activated form. The addition products of the 1,3-diene selected and the magnesium then form quickly and without there being any slowing up.

The molar ratio between the 1,3-diene used and the Mg used can preferably vary between 5:1 and 1:5. It is particularly preferable for the 1,3-diene:Mg ratio to be from 1:1 to 1:3. If a metal-free intermediate or end product is to be obtained, then, in this case, the soluble 1,3-diene/Mg addition product must be separated off from the excess Mg metal.

The solution of the 1,3-diene/Mg addition product which is obtained can be stored for from several weeks to months, if air and moisture are excluded.

To prepare an Mg alcoholate, the solution of the 1,3-diene/Mg addition product is mixed with the desired alcohol. The alcohol used can, for example, be isopropanol, tert. butanol, 2-ethyl hexanol or tert. pentanol. Preferably the addition product is provided and the alcohol is added in pure form or diluted with a solvent. The alcohol is preferably added in at least twice the molar quantity relative to the 1,3-diene/Mg addition product (hence in at least a stoichiometric quantity). The reaction is highly exothermic. The reaction temperature can be between 0 and 100° C. and preferably between 20 and 70° C. If the reaction is performed in slightly volatile solvents, such as THF for example, operations can take place under reflux conditions. The addition of the alcohol takes place in such a way that the heat generated can be safely dissipated, that is to say over between approx. 10 min, and 5 hours depending on the scale and the apparatus available. The insoluble alcoholate is separated off by filtration or centrifuging, washed, and then dried.

The typical yield of Mg alcoholate is >95% at a purity of between 90 and 99% (depending on the washing). The product is free of metal contamination and specifically the Li content is <100 ppm.

The preparation of the Mg alcoholate can also take place in the same reaction vessel, without the 1,3-diene/magnesium addition product having previously been isolated. In this variant of the method, the preferred molar ratio between the total quantity of 1,3-diene and the Mg is 5:1 to 1.5:1 and the particular preference is for 3:1 to 2:1, i.e. operations do not take place with an excess of Mg.

It is also possible for at least part of the preparation of the Mg alcoholate to take place simultaneously with the formation of further 1,3-diene/magnesium addition product. For this purpose the Mg metal is provided in the aprotic solvent and is first mixed with 5 to 99% of the total quantity of 1,3-diene. The addition can take place within a period ranging from a few minutes to up to approx. 2 hours. In this case too a polynuclear aromatic compound can be used as a catalyst. On completion of the first reaction phase, the alcohol required for the formation of the alcoholate is added in a mixture with the remaining amount of 1,3-diene within from 0.5 to 5 hours. Care must be taken in this case to see that the 1,3-diene/magnesium addition product is always present in excess with respect to the amount of alcohol measured in. If this is not the case, it is possible for the reaction to stop completely. A check can be made either visually (e.g. the reddish-orange colour of the anthracene/Mg adduct; this colour disappears when there is an excess of alcohol) or by spectroscopic methods (e.g. photometry or "inline-infrared"). With this in mind, the addition of the alcohol can also be controlled automatically. 1 to 50% of the total quantity of the 1,3-diene/magnesium addition product is preferably formed in the first reaction phase before the reaction to produce the Mg alcoholate is started by adding the alcohol. The magnesium alcoholate is formed in a highly exothermic reaction and surprisingly it first arises in soluble form. It is only towards the end of the measuring-in that the alcoholate begins to precipitate as a colourless finely divided solid, which is isolated in a normal way.

The Mg alcoholates prepared in this way can, for example, be used as catalysts in organic synthesis and they can preferably be used as condensing agents.

The subject matter of the invention will be explained in detail by reference to the following examples:

EXAMPLE 1

Preparation of Magnesium Tert. Butoxide by the "One-vessel Method"

9.0 g (370 mmol) of powdered magnesium (Timminco <150 µm) were suspended in 480 g of water-free THF in a 1 liter double-walled glass reaction vessel with a reflex cooler, internal thermometer and drip funnel and was mixed with 1.9 g (11 mmol, 3 mol %) of anthracene. The mixture was then heated to 50° C. After approximately 20 minutes the solution became orange in colour due to the formation of the Mg-anthracene adduct. 51 g (750 mmol) of isoprene were then dipped in within 10 min, and stirring took place for 1.5 hours at an internal temperature of between 50 and 55° C. A sample was taken and was titrated for total base content: the base content of 0.29 mmol/g was equivalent to reaction of approximately 21% of the total magnesium used. A mixture of 58 g of t-butanol (780 mmol) and 6 g of isoprene (90 mmol) was then added within 130 minutes. In the course of this care was taken to see that the colour deriving from the Mg-anthracene complex did not disappear.

The heat of reaction released heated the mixture to boiling point (59 to 65° C. depending on how far the reaction had progressed). A colourless solid began to precipitate after approximately ¾ of the quantity of alcohol had been added.

At the end of the addition, refluxing took place for a further 30 minutes and the reaction mixture was then drained onto a filter of fitted glass. The solid, colourless product was washed twice on the frit with hexane and was then vacuum-dried to a constant weight at ambient temperature.
Yield: 58.6 g (344 mmol, 93% of theoretical quantity)
Analysts: Total base: 11.0 mmol/g (11.7 theoretically) Mg: 5.51 mmol/g (5.86 theoretically)

Residues of Mg metal were no longer apparent in the product.

EXAMPLE 2

Preparation of the Soluble Isoprene/Mg Complex 92 g (3.78 mol) of powdered magnesium were suspended in 1090 g of THF in a 2 liter double-walled reaction vessel with a high-intensify reflux cooler, drip funnel and internal thermometer and were mixed with 1.0 g (6 mmol, 0.2 mol %) of anthracene. Refluxing was carried out until the reddish range colour of the anthracene complex could be seen (approx. 30 minutes) and cooling then took place to 40° C. At this temperature, 207 g (3.04 mol) of isoprene were dripped in within 40 min. On completion of the dripping-in, the jacket temperature was raised to 70° C. and refluxing took place for 5 hours accompanied by vigorous stirring. In the course of this the boiling point rose from 59 to 66° C.

Cooling then took place to approx. 40° C. and the suspension was filtered through a glass frit. The reaction vessel and frit were then flushed out with 100 g of THF.
Yield: 1419 g of greenish-yellow, slightly viscous solution
Analysis: Total base: 2.91 mmol/g The yield of 4129 mmol of base corresponded to 2065 mmol of soluble Mg/isoprene complex. It follows from this that there must have been approx. 36% of 1:1 complex present in addition to 64% of 2:1 adduct.

EXAMPLE 3

Preparation of Magnesium Tert. Butoxide from Isolated Mg/isoprene Adduct 634 g of the filtered solution from Example 2 (=922 mmol of Mg adduct) were provided in a 2 liter double-walled reaction vessel with a drip funnel, reflux cooler and internal thermometer at an internal temperature of 30° C. At a constant jacket temperature of 30° C., a mixture of 143.8 g (1.94 mol, 5% excess) of water-free tert. butanol mixed with 17 g of THF was measured in within 15 minutes. The reaction mixture then quickly heated up to boiling point (61° C.). On completion of the measuring-in, refluxing took place for 80 minutes. A white suspension formed and this was drained onto a fitter of fritted glass after cooling to 40° C. After the mother liquor had been removed, the solid white material retained by the filter was washed with three portions of hexane (each approx. 200 g).

The filter cake was then vacuum-dried first at ambient temperature and then at 60 to 90° C.

Yield: 155 g of fine, white powder (95% of theoretical quantity) Analysis Total base: 11.34 mmol/g $Mg^2$: 5.64 mmol/g

What is claimed is:

1. A method for preparing a magnesium alcoholate of the formula $Mg(OR)_2$ wherein R is a $C_2$–$C_{10}$ alkyl group comprising:
    reacting a 1,3-diene/magnesium metal addition product together with an alcohol of formula R—OH in a polar, aprotic solvent; wherein R is a $C_2$–$C_{10}$ alkyl group to form the magnesium alcoholate of formula $Mg(OR)_2$.

2. The method according to claim 1, wherein said 1,3-diene/magnesium metal addition product is prepared by reacting a 1,3-diene with magnesium metal in a polar, aprotic solvent, and further comprising the steps of isolating said 1,3-diene/magnesium addition product and at a later point in time reacting said 1,3-diene/magnesium addition product with said alcohol in said polar, aprotic solvent to form said magnesium alcoholate.

3. The method according to claim 1, wherein said 1,3-diene/magnesium addition product is prepared by reacting magnesium metal and a 1,3-diene in a polar, aprotic solvent in reaction vessel, wherein the reaction of the 1,3-diene/magnesium addition product with said alcohol to form the magnesium alcoholate takes place in the same reaction vessel.

4. The method according to claim 3, wherein at least part of the formation of said magnesium alcoholate occurs simultaneously with formation of said 1,3-diene/magnesium addition product.

5. The method according to claim 4, wherein after from 1 to 50% of the total quantity of said 1,3-diene/magnesium addition product has formed, the reaction of said 1,3-diene/ magnesium addition product to produce said magnesium alcoholate is initiated by adding said alcohol to said reaction vessel.

6. The method according to claim 1, wherein the 1,3-diene is selected from the group consisting of 1,3-butadiene, isoprene, dimethyl butadiene and 1,3-cyclohexadiene.

7. The method according to claim 1, wherein the polar, aprotic solvent is an ether.

8. The method according to claim 7, wherein said ether is at least one ether selected from the group consisting of tetrahydrofuran, 2-methyl tetrahydrofuran, dimethyl ether and 1,3-dimethoxyethane.

9. The method according to claim 1, wherein the polar, aprotic solvent comprises a liquid hydrocarbon.

10. The method according to claim 2, wherein the formation of said 1,3-diene/magnesium addition product is catalyzed by a polynuclear aromatic compound.

11. The method according to claim 10, wherein said polynuclear aromatic compound is selected from the group consisting of anthracene, phenanthrene and biphenyl.

12. The method according to claim 10, wherein said polynuclear aromatic compound is added in a quantity of 0.01 to 5 mol % relative to the moles of magnesium.

13. The method according to claim 1, wherein said alcohol is selected from the group consisting of isopropanol, tent-butanol, 2-ethyl hexanol and tert-pentanol.

14. The method according to claim 13, wherein said 1,3-diene/magnesium addition product is prepared by reacting magnesium metal with a 1,3-diene in a polar, aprotic solvent.

15. The method according to claim 14, wherein at least part of the formation of said magnesium alcoholate takes place simultaneously with formation of 1,3-diene/ magnesium addition product.

16. The method according to claim 14, wherein after from 1 to 50% of the total quantity of the 1,3-diene/magnesium addition product has formed, the reaction of said 1,3-diene/magnesium addition product to produce said magnesium alcoholate is started by adding said alcohol to said reaction vessel.

17. The method according to claim 14, wherein the 1,3-diene is selected from the group consisting of 1,3-butadiene, isoprene, dimethyl butadiene and 1,3-cyclohexadiene.

18. The method according to claim 14, wherein the polar, aprotic solvent is an ether.

19. The method according to claim 18, wherein said ether is at least one ether selected from the group consisting of tetrahydrofuran, 2-methyl tetrahydrofuran, dimethyl ether and 1,3-dimethoxyethane.

20. The method according to claim 14, wherein the polar, aprotic solvent comprises a liquid hydrocarbon.

* * * * *